United States Patent [19]

Shimamura et al.

[11] Patent Number: 5,644,050

[45] Date of Patent: Jul. 1, 1997

[54] METHOD FOR MANUFACTURING LACTULOSE ANHYDRIDE

[75] Inventors: Seiichi Shimamura; Yoshitaka Tamura; Teruhiko Mizota; Itsuko Suzawa; Nobuo Seki, all of Kanagawa, Japan

[73] Assignee: Morinaga Milk Industry Co., Ltd., Tokyo, Japan

[21] Appl. No.: 500,858

[22] PCT Filed: Jun. 22, 1993

[86] PCT No.: PCT/JP93/00841

§ 371 Date: Sep. 1, 1995

§ 102(e) Date: Sep. 1, 1995

[87] PCT Pub. No.: WO94/18213

PCT Pub. Date: Aug. 18, 1994

[30] Foreign Application Priority Data

Feb. 2, 1993 [JP] Japan .................................... 5-015736

[51] Int. Cl.$^6$ .............................. C13K 13/00; C07H 1/00
[52] U.S. Cl. ........................................ 536/123.13; 536/124
[58] Field of Search ............................... 536/123.13, 124

[56] References Cited

U.S. PATENT DOCUMENTS 4,536,221 8/1985 Carobbi et al. ..................... 536/127

FOREIGN PATENT DOCUMENTS 5111400 5/1993 Japan.

OTHER PUBLICATIONS

*Carbohydrate Rearch*, vol. 226, issued 1992, Jeffrey et al, "Crystal Structure and n.m.r. Analysis of Lactulose Trihydrate", pp. 29–42.

*Primary Examiner*—John Kight
*Assistant Examiner*—Everett White
*Attorney, Agent, or Firm*—Wenderoth, Lind & Ponack

[57] ABSTRACT

The present invention provides a method for manufacturing lactulose anhydride, which comprises drying lactulose trihydrate at a temperature within a range of from 45° to 75° C. and a degree of vacuum within a range of from 25 to 100 Torr to remove water of crystallization.

The method of the present invention permits manufacture of lactulose anhydride through a simple process, at a high yield and at a low cost, and is therefore suitable for mass production of lactulose anhydride in an industrial scale.

2 Claims, No Drawings

METHOD FOR MANUFACTURING LACTULOSE ANHYDRIDE

TECHNICAL FIELD

The present invention relates to a method for manufacturing lactulose anhydride. More particularly, the present invention relates to a method for mass production of lactulose anhydride useful as a growth factor of Bifidobacterium, a medical drug for hepatic encephalopathy and the like, simply and at a low cost.

BACKGROUND ART

Upon discovery, lactulose had been prepared from an alcoholic solution in the form of anhydrous lactulose crystal (hereinafter sometimes referred to as "anhydride") [Journal of American Chemical Society, Vol. 52, p. 2101, 1930]. Since then, lactulose has been believed to be prepared by forming an anhydride. More recently, it was reported that lactulose trihydrate crystal (hereinafter sometimes referred to as "hydrate") was available from an aqueous solution [Carbohydrate Research, Vol. 6, p. 29, 1992].

As lactulose is a substance useful as a growth promoting factor of Bifidobacterium and a medical drug for hepatic encephalopathy, various manufacturing methods have so far been developed.

When manufacturing lactulose, obtaining a hydrate from an aqueous solution is preferable to obtaining an anhydride from an alcoholic solution, from the points of view of simplicity, safety and economic advantages.

Lactulose is on the other hand commercially produced in the form of a syrup or powder. For the convenience in handling, commercial production in a powdery form is preferable. Lactulose is not however suitable for producing into a powdery product because of a high water-solubility, and particularly such a low melting point as 68.1° C. of the hydrate, resulting in melting at a temperature of about 58° to 60° C.

The anhydride has in contrast such a high melting point as 169° C. and is stable even in a powdered state, leading to an important value of use. There is therefore an increasing demand for a manufacturing method which is safe and simple as that of the hydrate.

From such a point of view as described above, the present inventors invented a method for converting a hydrate into an anhydride, and filed an application for a patent under the title of a method for manufacturing crystalline lactulose anhydride (Japanese Patent Application No. 03-272,841; Japanese Patent Provisional Publication No. 05-111,400; hereinafter referred to as the "prior application"). The method of this prior application comprises the steps of drying crystalline lactulose trihydrate dried at the room temperature, under the atmospheric pressure and at a temperature within a range of from 45° C. to the melting point, and then drying same at a temperature of up to 80° C.

The method of the prior application has made it possible to eventually obtain lactulose anhydride from an aqueous solution, not from an alcoholic solution, as described above.

Even in this excellent method of the prior application, however, there still remain problems to be solved before application in an industrial scale. More specifically, the method of the prior application has drawbacks in that, since crystalline lactulose trihydrate is dried by, for example, the fluidized-bet drying method, crystalline lactulose fines scatter, resulting in a decrease in the final product yield, and that the fluidized-bet drier is large in size and high in cost.

DISCLOSURE OF INVENTION

The present invention has an object to provide a novel method which permits manufacture of lactulose anhydride by a simple process, at a high yield and at a low cost by improving the method of the prior application described above while retaining the favorable features of the latter.

As a mean for achieving the above-mentioned object, the present invention provides a method for manufacturing lactulose anhydride, which comprises drying lactulose trihydrate at a temperature within a range of from 45° to 75° C. and at a degree of vacuum within a range of from 25 to 100 Torr to remove water of crystallization.

A preferred embodiment of the method of the present invention comprises starting drying of lactulose trihydrate at a temperature within a range of from 45° to 60° C. and at a degree of vacuum within a range of from 30 to 60 Torr while stirring the trihydrate, then gradually heating the trihydrate, and removing water of crystallization while stirring at a temperature within a range of from 60° to 70° C. and at a degree of vacuum within a range of from 30 to 60 Torr.

The method of the present invention as described above makes it possible to convert hydrate into anhydride keeping a powdery state, and to manufacture lactulose anhydride at a high yield by a simple process comprising heating and pressure reduction without using a solvent such as alcohol at all for removing water of crystallization. The method of the present invention is suitable for industrial application because of the possibility of easily expanding the scale, and is economically advantageous because of the use of a compact and inexpensive facility.

BEST MODE FOR CARRYING OUT THE INVENTION

The same hydrate not as yet dried as in the prior application can be used as the starting material for the method of the present invention, an example of which is as follows.

The lactulose syrup used in the manufacture of the hydrate may be one manufactured by a known method (for example, Japanese Patent No. 874,954), or a commercially available one. In addition to water, the lactulose syrup usually contains 45 to 55% (weight percentage; the same applies also hereafter unless otherwise specified) lactulose, 2 to 8% galactose, 2 to 5% lactose, and 2 to 8% other sugars, with a purity of lactulose in solids of from 70 to 90%. This usual lactulose syrup may be directly used without purifying. With a lactulose concentration of under 70% in solids, substances other than lactulose are more liable to crystallize, and separation of hydrate becomes difficult.

Since the lactulose syrup contains lactose having a low solubility, lactose crystals should preferably be removed as far as possible in order to obtain a hydrate. For this purpose, the sugar-in-water ratio of lactose [lactose content/(lactose content+water content)] is kept below 10%, and total solids are concentrated to 65 to 75%. With a total solid concentration of under 65%, lactulose is not supersaturated, resulting in no precipitation of hydrate or in a precipitation at a low yield. A total solid concentration of over 75% leads in contrast to a high viscosity of the lactulose syrup which is difficult to handle.

Then, the concentrated lactulose syrup is cooled to a temperature of from 2° to 20° C. and seed crystals are added (seeding) for lactulose and stirred to cause precipitation of crystals. The temperature of crystal precipitation should preferably be the lowest possible, and larger crystal should be precipitated through slow cooling. A hydrate is desirable as lactulose for seeding. Crystals of hydrate are sufficiently caused to grow, and then the hydrate is separated by a known method (for example, the centrifugal filtration method or the decantation method). The separated hydrate is washed with water to remove impurities. Considering the high solubility of hydrate, washing should preferably be conducted with the smallest possible amount of cold water. Because the resultant hydrate is in a state wetted with water, it is necessary to remove water from the surface. When the hydrate contains free water, the hydrate is dried at the room temperature under the atmospheric pressure or under vacuum to substantially eliminate free water, and then the resultant dried hydrate is used as the starting material in the present invention.

In the method of the present invention, as will be clear from a test example described later, an anhydride is available by drying the hydrate at a temperature within a range of from 45° to 75° C. and at a degree of vacuum within a range of from 25 to 100 Torr and eliminating water of crystallization. The anhydride is available under any conditions within the above-mentioned ranges of conditions, whereas more preferable manner comprises the steps of, first, starting drying of the hydrate at a temperature within a range of from 45° to 60° C. and at a degree of vacuum within a range of from 30 to 60 Torr while stirring, then gradually heating the dried hydrate, continuing drying at a temperature of from 60° to 75° C. and a degree of vacuum of from 30 to 60 Torr while stirring, and thus almost completely eliminating water of crystallization from the hydrate, whereby an anhydride is available. The heating rate, which may be arbitrarily selected as a rule, should more preferably be within a range of from 0.2° to 0.6° C./minute.

An anhydride is a substance available by removing water of crystallization from a hydrate. There is therefore conceivable a general drying method using drying by heating or vacuum drying. It is however difficult to practically carry out these methods. This will be proved below by showing Tests in which an anhydride obtained by these general methods is compared with an anhydride available by the method of the present invention.

Test 1

A hydrate prepared by the same method as in the Example 1 (melting starting point: 58° to 60° C.) was dried at a temperature of 60° C. under one of the following values of pressure for six hours. The results of measurement of properties of the resultant samples are shown in Table 1.

Sample 1-1: Atmospheric pressure, using a drier (purchased from Toyo Seisakusho);

Sample 1-2: Under vacuum of 30 Torr, using a vacuum drier (purchased from Yamato Kagaku Co.);

Sample 1-3: Under vacuum of 4 Torr, using a vacuum drier (purchased from Yamato Kagaku Co.).

As is clear from the results shown in Table 1, in the case of drying under the atmospheric pressure which is a general drying method (Sample No. 1-1), crystals melt in the form of small jelly-like balls adhering onto the wall and dried. After leaving in the open air after drying, these balls melt in a honey-like mass by absorbing moisture in the air, thus making it impossible to obtain a stable anhydride. In the case of drying under a high vacuum which is another general drying method (4 Torr)(Sample No. 1-3), crystals are dried into powder. After leaving in the open air after drying, the sample showed a strong hygroscopicity, losing fluidity, and showed a change in the form of partial deliquescence, thus making it impossible to obtain a stable anhydride.

In contrast, the powder of the method of the present invention obtained through drying under vacuum of 30 Torr (Sample No. 1-2), unlike the other powder samples, showed no change after leaving in the open air after drying, and exhibited a melting point within a range of from 167° to 169° C.

It is evident from these results that a stable anhydride is unavailable when a hydrate is dried by heating under the atmospheric pressure or dried under a high vacuum, and a stable anhydride is available only when the hydrate is dried under vacuum of 30 Torr according to the method of the present invention.

TABLE 1

| Sample No. | 1-1 | 1-2 | 1-3 |
|---|---|---|---|
| Exterior view after drying for 6 hr. | Powder melts and firmly adheres to the container wall | Powdery | Powdery |
| Loss on drying (%) | 9.8% | 13.0% | 13.2% |
| Exterior view after leaving in open air for 18 hr. | Melting into honey-like state | No change | Fluidity lost, and partial deliquescence |
| Melting point (°C.) |  | 167–169 |  |

With reference to the results of the above-mentioned Test 1, the following test was carried out to more clearly determining appropriate temperature and degree of vacuum for drying.

Test 2

The Test 2 comprised the steps of putting 10 g accurately weighed hydrate prepared by the same method as in the Example 1 in a glass beaker, placing the hydrate in a vacuum drier (purchased from Yamato Kagaku Co.), drying the hydrate at a temperature within a range of from 40° to 80° C. and at a degree of vacuum within a range of from 4 to 560 Torr for six hours, measuring the weight loss ratio as an indicator of the conversion efficiency from hydrate to anhydride, leaving the dried sample in the open air for 24 hours, measuring hygroscopicity, exterior view and melting point thereof. The results are shown in Table 2.

At a temperature of 40° C., as is clear from Table 2, the weight loss ratio is so small that conversion from hydrate to anhydride does not progress efficiently. This is not therefore practical at all. A temperature of 80° C. is not desirable because the resultant powder exhibits a tendency toward becoming brownish in color.

A degree of vacuum of up to 20 Torr is not desirable since hygroscopic tendency after drying is remarkable, leading to tendency toward deliquescence and solidification. Conditions including 75° C. and 160 Torr, and 60° C. and 560 Torr are not desirable in that the powder partially melt, becoming a honey-like dried product, with a small weight loss ratio.

By drying the hydrate at a temperature within a range of from 45° to 75° C. and a degree of vacuum within a range of from 25 to 100 Torr, there is available a stable powder free from hygroscopicity, with a melting point of from 167° to 169° C., showing the same value as that of the anhydride. The present invention is therefore applicable within this range. When drying is conducted under a low vacuum as 100 Torr, however, the poor water removing ability requires, in the case of drying with an increased amount of hydrate, much more time for drying, or the high temperature for drying results in an increased content of free water, results in mutual bonding of crystals, and then leads to a tendency of easily forming lumps. It is therefore particularly recommendable to carry out drying under vacuum of from 30 to 60 Torr.

When drying is carried out at a temperature of over 60° C. in the initial stage of drying, crystals tend to melt and adhere to the container wall. It is therefore particularly recommended to conduct drying at a starting temperature within a range of from 45° to 60° C., gradually increasing temperature, and finally at a temperature within a range of from 60° to 75° C.

Another preferable practice is to improve heat conduction, sufficiently drying the hydrate as a whole, and carrying out drying while stirring the hydrate under the above-mentioned conditions of vacuum and temperature to inhibit adherence of powder.

cloth type centrifugal separator (purchased from Kokusan Enshinki Co.). The separated crystals were washed with cold water at 5° C., thus obtaining about 22.5 kg hydrate crystals. The resultant hydrate crystals were dried at a temperature of 30° C. for eight hours by means of a vacuum drier (purchased from Kyowa Shinku Co.), thus obtaining about 20.8 kg dried crystals.

The thus obtained dried crystals had the following physical and chemical properties:

1) Water content:
Water content based on the Karl Fischer's method: 14.0%
Water content lost on diphosphorus pentoxide at the room temperature: 0.3%

TABLE 2

| Drying temp. (°C.) | | Degree of vacuum (Torr) | | | | | | |
|---|---|---|---|---|---|---|---|---|
| | | 4 | 20 | 25 | 30 | 50 | 100 | 160 | 560 |
| 40 | A | | | | 2.1 | | | | |
| | B | | | | 0 | | | | |
| | C | | | | Powdery | | | | |
| | D | | | | | | | | |
| 45 | A | | | | 12.8 | 12.8 | | 12.5 | |
| | B | | | | 0.2 | 0 | | 0.1 | |
| | C | | | | Powdery | Powdery | | Powdery | |
| | D | | | | 167–169 | 167–169 | | 167–169 | |
| 60 | A | 13.0 | 13.5 | | 13.2 | 13.0 | 13.0 | 12.8 | 13.4 | 6.8 |
| | B | 7.5 | 5.4 | | 0.2 | 0 | 0.1 | 0 | 0.2 | –4.1 |
| | C | Partial deliquescence, solidification | Partial deliquescence, solidification | | Powdery | Powdery | Powdery | Powdery | Powdery | Partial honey-like, adhering and solidifying |
| | D | | | | 167–169 | 167–169 | 167–169 | 167–169 | 167–169 | |
| 70 | A | | | | 13.0 | 13.0 | | 12.8 | | |
| | B | | | | 0.1 | 0 | | 0 | | |
| | C | | | | Powdery | Powdery | | Powdery | | |
| | D | | | | 167–169 | 167–169 | | 167–169 | | |
| 75 | A | | | | 13.0 | 12.9 | | 12.8 | 10.2 | |
| | B | | | | 0.2 | 0.1 | | 0.1 | –0.2 | |
| | C | | | | Powdery | Powdery | | Powdery | Partial honey-like, adhering and solidifying | |
| | D | | | | 167–169 | 167–169 | | 167–169 | | |
| 80 | A | | | | 12.5 | | | | | |
| | B | | | | 0.5 | | | | | |
| | C | | | | Slightly brownish | | | | | |
| | D | | | | | | | | | |

(Note)
A: Weight loss ratio (%) after drying for six hours.
B: Hygroscopicity (%) after leaving in the open air for 24 hours.
C: Exterior view after leaving in the open air for 24 hours.
D: Melting point (°C.) after leaving in the open air for 24 hours.

Now, the present invention is described further in detail by means of a few examples. However the present invention is not limited to the following examples.

EXAMPLE 1

Lactulose syrup (made by Morinaga Milk Industry Co., Ltd; comprising, in solids, 85.6% lactulose, 3.1% lactose, 5.2% galactose, and 6.1% other sugars) was concentrated to a sugar-in-water ratio of 7.9% and a total solid content of 71.8%. The resultant concentrated liquid in an amount of 100 kg was cooled to 15° C., and 300 g hydrate was added for seeding. The mixture was slowly cooled to 5° C. spending for seven days while stirring, to prepare hydrate crystals. After the lapse of ten days, crystals were separated from the solution containing crystals of which the solid content of the supernatant liquid decreased to 61.3% by means of a filter 2) Lactulose quantitative assay value:
Quantitative assay value by liquid chromatography based on the method set out in the United States Pharmacopeia: Twenty-second Revision Supplement 1, p. 2138, The United States Pharmacopeia Convention, Inc.: 85.9%
Calculated hydrate in the material dried over diphosphorus pentoxide at room temperature: 99.7%

3) Starting point of melting:
Value measured by the capillary method: 58° to 60° C.

This dried hydrate crystal in an amount of 5.0 kg was placed in a vacuum concentrator (purchased from Mizuho Kogyo Co.), and dried at a temperature of 60° C. and a degree of vacuum of 30 Torr for eight hours while stirring, resulting in about 4.1 kg anhydride.

The resultant anhydride was stable as typically represented by a hygroscopicity of 0% after leaving in the open air for 24 hours, and had the following property values:

1) Lactulose content:

Quantitative assay value by the same method as above: 99.1%

2) Water content:

After drying at 105° C. for five hours: 0.8%

3) Melting point:

Measured value by the same method as above: 167° to 169° C.

EXAMPLE 2

The dried hydrate crystals obtained in the Example 1 in an amount of 5.0 kg were put in a vacuum concentrator (purchased from Mizuho Kogyo Co.), stirred at a temperature of 50° C. under a vacuum of 50 Torr for one hour, and then continuously dried at a temperature of 70° C. under a vacuum of 30 Torr for another four hours while stirring, resulting in about 4.1 kg anhydride.

The resultant anhydride was stable as represented by a hygroscopicity of 0% after leaving in the open air for 24 hours, and had the following property values:

1) Lactulose content:

Quantitative assay value by the same method as above: 99.2%

2) Water content:

Assay value by the same method as above: 0.6%

3) Melting point:

Measured value by the same method as above: 167° to 169° C.

EXAMPLE 3

The dried hydrate crystal grains obtained in the Example 1 in an amount of 500 g were spread over a tray, and dried at a temperature of 55° C. under a vacuum of 100 Torr for 15 hours by means of a vacuum concentrator (made by Yamato Kagaku Co.), giving about 430 g anhydride.

The thus obtained anhydride was stable as represented by a hygroscopicity of 0% after leaving in the open air for 24 hours, and had the following property values:

1) Lactulose content:

Assay value by the same method as above: 99.1%

2) Water content:

Assay value by the same method as above: 0.8%

3) Melting point:

Measured value by the same method as above: 167° to 169° C.

Industrial Applicability

The method of the present invention is suitable for mass production in an industrial scale of lactulose anhydride useful as a growth promoting factor of Bifidobacterium and a medical drug for hepatic encephalopathy.

We claim:

1. A method for manufacturing lactulose anhydride, which comprises drying lactulose trihydrate at a temperature within a range of from 45° to 75° C. and a degree of vacuum within a range of from 25 to 100 Torr to remove water of crystallization.

2. A method for manufacturing lactulose anhydride as claimed in claim 1, which comprises starting drying the lactulose trihydrate at a temperature within a range of from 45° to 60° C. and a degree of vacuum within a range of from 30 to 60 Torr while stirring, gradually heating the trihydrate, and removing water of crystallization while stirring the trihydrate at a temperature within a range of from 60° to 70° C. and a degree of vacuum within a range of from 30 to 60 Torr.

* * * * *